United States Patent
Funke et al.

(10) Patent No.: US 9,056,848 B2
(45) Date of Patent: Jun. 16, 2015

(54) PROCESS FOR PREPARING SODIUM SALTS OR POTASSIUM SALTS OF 4-HYDROXY-2-OXO-2,5-DIHYDROFURAN-3-CARBOXYLATE

(75) Inventors: Christian Funke, Leichlingen (DE); Taraneh Farida, Pulheim-Geyen (DE); Stefan Beeck, Meerbusch (DE); Norbert Lui, Odenthal (DE); Berndt Maiwald, Burschied (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/002,695

(22) PCT Filed: Feb. 29, 2012

(86) PCT No.: PCT/EP2012/053418
§ 371 (c)(1),
(2), (4) Date: Oct. 31, 2013

(87) PCT Pub. No.: WO2012/117015
PCT Pub. Date: Sep. 7, 2012

(65) Prior Publication Data
US 2014/0148604 A1 May 29, 2014

Related U.S. Application Data

(60) Provisional application No. 61/448,805, filed on Mar. 3, 2011.

(30) Foreign Application Priority Data

Mar. 3, 2011 (EP) ..................................... 11156806

(51) Int. Cl.
C07D 307/00 (2006.01)
C07D 307/60 (2006.01)
C07D 307/68 (2006.01)

(52) U.S. Cl.
CPC ............ C07D 307/60 (2013.01); C07D 307/68 (2013.01)

(58) Field of Classification Search
None
See application file for complete search history.

(56) References Cited

U.S. PATENT DOCUMENTS

| | | | |
|---|---|---|---|
| 6,172,257 B1 | 1/2001 | Muhr et al. | |
| 8,273,904 B2 * | 9/2012 | Lui et al. | ........................ 549/322 |
| 8,318,955 B2 | 11/2012 | Lui et al. | |
| 2010/0190990 A1 | 7/2010 | Lui et al. | |
| 2011/0060147 A1 | 3/2011 | Lui et al. | |
| 2012/0323023 A1 | 12/2012 | Lui et al. | |

FOREIGN PATENT DOCUMENTS

| | | |
|---|---|---|
| EP | 0950623 | 10/1999 |
| WO | 2008150487 | 12/2008 |
| WO | 2009036899 | 3/2009 |
| WO | WO 2009036899 A1 * | 3/2009 |
| WO | 2011018180 | 2/2011 |

OTHER PUBLICATIONS

Campbell, AC. et al. Synthesis of (E)- and (Z)- Pulvinones. J. Chem. Soc. Perkin Trans. 1985, vol. 1, p. 1571, scheme 4, p. 15-70.*
Breslow, DS. et al. A New Synthesis of β-Keto Esters of the Type RCOCH2COOC2H5. Journal of the American Chemical Society. 1944, vol. 66, p. 1287.*
Goldman, IM. Activation of Manganese Dioxide by Azeotropic Removal of Water. Tetrahedron. 1969, vol. 34, p. 1979.*
International Search Report for PCT/EP2012/053418 Mailed Mar. 26, 2012.
Benary, "The Action of Halo-Fatty Acid Halides on Malonates," Berichte d. D. Chem Gesellschaft, vol. 44, pp. 1759-1765, (1911).
Breslow, "A New Synthesis of Beta-Keto Esters of the Type RCOCH2COOC2H5," J. Am Chem. Soc., vol. 66, pp. 1286-1288 (1944).
Campbell et al., "Synthesis of (E)- and (Z)- Pulvinones," J. Chem. Soc. Perkin Trans. 1, pp. 1567-1576, (1985).

* cited by examiner

*Primary Examiner* — Janet L Andres
*Assistant Examiner* — Ben S Michelson
(74) *Attorney, Agent, or Firm* — Miles & Stockbridge P.C.

(57) ABSTRACT

Process for preparing sodium or potassium salts of 4-hydroxy-2-oxo-2,5-dihydrofuran-3-carboxylic esters, comprising the reaction of a malonic ester with potassium hydroxide to give the corresponding malonic ester potassium salt of the formula (III)

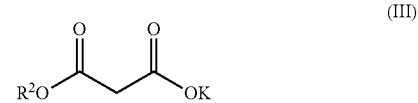

which is then reacted further with a chloroacetic ester to give a compound of the formula (V)

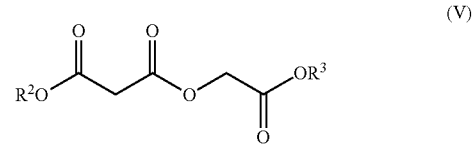

followed by a ring closure reaction in which the compound of the formula (V) is reacted with a sodium or potassium alkoxide of the formula $ZOR^1$ where $R^1$, $R^2$, $R^3$ and K are each as defined in the description.

13 Claims, No Drawings

PROCESS FOR PREPARING SODIUM SALTS OR POTASSIUM SALTS OF 4-HYDROXY-2-OXO-2,5-DIHYDROFURAN-3-CARBOXYLATE

CROSS REFERENCE TO RELATED APPLICATIONS

This application is a §371 National Stage Application of PCT/EP2012/053418, filed Feb. 29, 2012, which claims priority to European Application No. 11156806.9, filed Mar. 3, 2011, and U.S. Provisional Application No. 61/448,805, filed Mar. 3, 2011.

BACKGROUND OF THE INVENTION

1. Field of the Invention

The present invention relates to a process for preparing sodium or potassium salts of 4-hydroxy-2-oxo-2,5-dihydrofuran-3-carboxylic esters proceeding from malonic esters.

2. Description of Related Art

The preparation of hydroxy-2-oxo-2,5-dihydrofuran-3-carboxylic esters, the corresponding tautomers or the alkali metal salts thereof, and also the use thereof as a component in the synthesis of biologically active compounds, is known (WO 2011/018180, WO 2009/036899, J. Chem. Soc., Perkin Trans. 1, 1985, pages 1567 to 1576, Berichte der Deutschen Chemischen Gesellschaft (1911), 44, 1759-1765). However, the known processes have disadvantages as described hereinafter.

WO 2011/018180 describes the preparation of hydroxy-2-oxo-2,5-dihydrofuran-3-carboxylic ester and proceeds from malonic ester in the synthesis described therein. The latter is reacted with a haloacetyl chloride compound in the presence of a base (see reaction scheme 1). After addition of water, the desired 4-hydroxy-2-oxo-2,5-dihydrofuran-3-carboxylic ester is obtained. The base is selected so as to be capable of deprotinating the malonic ester, as a result of which the enolate of the malonic ester is formed, which is then acetylated by the haloacetyl chloride compound. Suitable bases are especially alkoxides of the general formula $M(OR^a)_b$, in which M is $Na^+$, $K^+$, $Mg^{2+}$, $b$ is 1 or 2 and $R^a$ is methyl or ethyl. Sodium methoxide is specified as preferred. On completion of ring closure, the desired product is obtained together with an inorganic salt which is obtained as a by-product (e.g. NaCl if a sodium alkoxide is used as the base).

Reaction scheme 1:

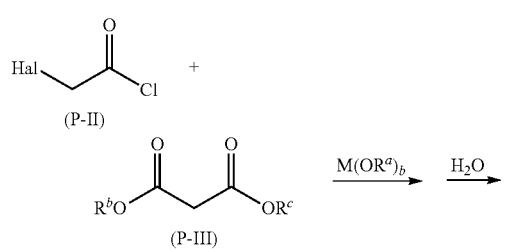

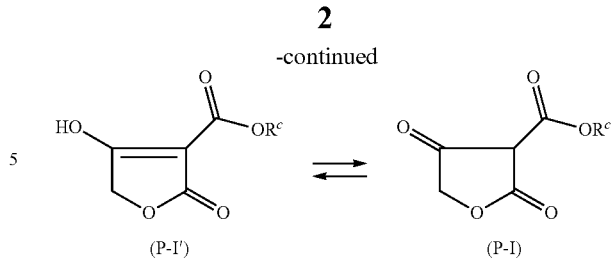

The removal of the inorganic salt from the reaction mixture, especially when it is NaCl, is achievable only through a very high level of technical complexity, if at all, since the compounds of the formula (P-I) and (P-I') are of very good water solubility. Distillation is impossible since the compounds of the formula (P-I) and (P-I') decompose at relatively high temperatures with release of $CO_2$. The inorganic salt is therefore not removed. It is introduced into the subsequent reaction and can only be removed on completion of further reaction of the compounds of the formula (P-I) and/or (P-I').

WO 2009/036899 describes the synthesis of salts of 4-hydroxy-2-oxo-2,5-dihydrofuran-3-carboxylic esters, which proceeds from malonic ester potassium salt and in which the corresponding salt of the 4-hydroxy-2-oxo-2,5-dihydrofuran-3-carboxylic ester is prepared using chloroacetic ester and an alkoxide base, e.g. sodium methoxide (see reaction scheme 2). This reaction does not give rise to any inorganic salts which have to be carried onward, but the reaction uses dimethylformamide or dimethylacetamide as a solvent, which are firstly expensive and secondly difficult to remove and recoverable only with difficulty.

Reaction scheme 2:

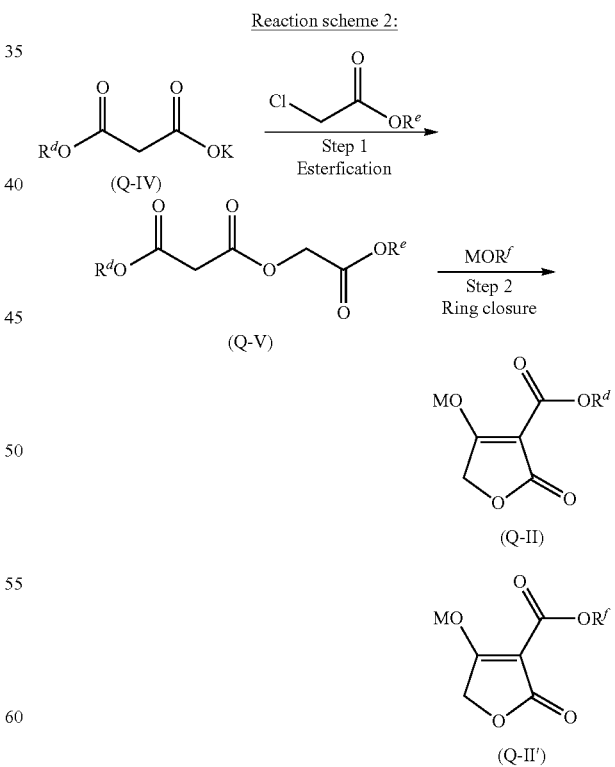

Step 1 of the aforementioned reaction is an esterification in which potassium chloride is obtained as a by-product and subsequently has to be separated from the reaction mixture. In step 2, the ring closure to give the desired compound (Q-II)

takes place, and a transesterification may occur therein, which results in isolation of a compound of the formula (Q-II'). The transesterification in step 2 can be suppressed by using alkoxides which contain sterically demanding R$^f$ radicals (for example a tert-butyl alkoxide). Compounds of the formula (Q-IV) are solids, are commercially available or can be prepared by known processes (cf. J. Am. Chem. Soc. 1944, No. 66, page 1286, EP-A-950653, WO 2008/150487).

The reaction is disadvantageous for industrial scale use since it proceeds from expensive malonic ester potassium salts of the formula (Q-IV) present in solid form. In the case of industrial scale preparation, the use of solids as starting materials is fundamentally undesirable since the technical handling of such solids is difficult and there are often changes of solvents, which leads overall to considerable technical complexity in the performance of the reaction.

SUMMARY

Proceeding from the known processes for preparing salts of 4-hydroxy-2-oxo-2,5-dihydrofuran-3-carboxylic esters or the corresponding enol tautomers, the problem now arises of preparing these in a simple and inexpensive manner, in such a way that the process can also be used for industrial scale preparation of the desired compound. It would also be desirable to find a process which at least partly proceeds continuously and in which complex isolations of the intermediates are avoided. Inexpensive processes are understood to mean those processes which are performable without any great financial expenditure because the starting materials are, for example, inexpensive and/or nonhazardous, the process needs few process steps or is even performable as a "one-pot reaction" (i.e. without any need for isolation of intermediates), and/or the desired sodium or potassium salt of the 4-hydroxy-2-oxo-2,5-dihydrofuran-3-carboxylic esters is obtained in a sufficiently high yield and purity. It is also advantageous to provide a process which is protective of resources, in which, for example, less energy is consumed and/or is selective, which means that by-products form only to a minor degree.

A process has now been found for preparing sodium or potassium salts of 4-hydroxy-2-oxo-2,5-dihydrofuran-3-carboxylic esters of the general formula (I), which avoids the aforementioned disadvantages and is performable in a simple and inexpensive manner, especially because it does not need complex isolation and/or purification of intermediates. Nor is any solid used as the starting material, and it is possible to dispense with expensive and inconvenient solvents. The process can proceed either continuously or batchwise.

It is known that hydroxy-2-oxo-2,5-dihydrofuran-3-carboxylic esters may also be present as tautomers, namely in the form of 2,4-dioxotetrahydrofuran-3-carboxylic esters. Any reference to hydroxy-2-oxo-2,5-dihydrofuran-3-carboxylic esters also includes the corresponding tautomer.

The invention thus provides the process described hereinafter for preparing sodium or potassium salts of 4-hydroxy-2-oxo-2,5-dihydrofuran-3-carboxylic esters of the formula (I)

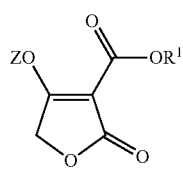
(I)

in which Z is sodium or potassium and R$^1$ is as defined hereinafter, and which, as already described, may be present in the following tautomeric forms:

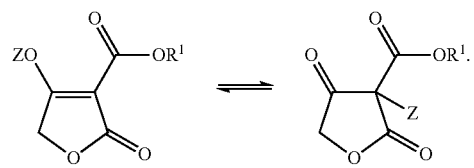

The application accordingly relates to a process for preparing sodium or potassium salts of 4-hydroxy-2-oxo-2,5-dihydrofuran-3-carboxylic esters of the formula (I), comprising the following steps:

Step (i):

reacting a symmetric malonic ester of the formula (II)

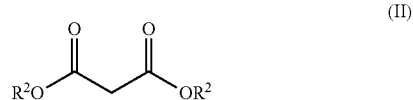
(II)

with potassium hydroxide which is preferably used in the form of an aqueous potassium hydroxide solution, to give the corresponding malonic ester potassium salt of the formula (III)

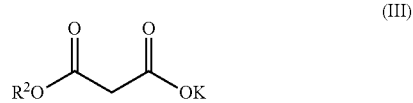
(III)

in which, in the formulae (II) and (III),

R$^2$ is C$_1$-C$_{12}$-alkyl, R$^2$ is preferably C$_1$-C$_4$-alkyl, R$^2$ is more preferably methyl or ethyl, in a solvent, preferably an alcohol, especially methanol or ethanol;

Step (ii):

reacting the malonic ester potassium salt of the formula (III) with a chloroacetic ester of the formula (IV)

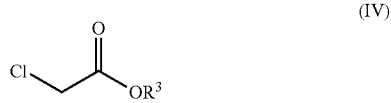
(IV)

in which

R$^3$ is C$_1$-C$_{12}$-alkyl, R$^3$ is preferably C$_1$-C$_4$-alkyl, R$^3$ is more preferably methyl or ethyl, to give a compound of the formula (V)

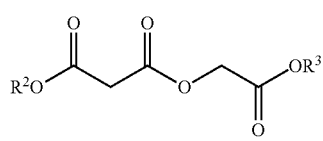
(V)

in which

R$^2$ has the definitions listed in relation to formula (III), and

R$^3$ has the definitions listed in relation to formula (IV),

Step (iii) Ring Closure Reaction:
reacting the compound of the formula (V) with a sodium or potassium alkoxide of the formula $ZOR^1$ in which
$R^1$ is $C_1$-$C_{12}$-alkyl, le is preferably $C_1$-$C_6$-alkyl, $R^1$ is more preferably ethyl or methyl, and
Z is sodium or potassium, preferably sodium,
wherein after addition of the chloroacetic ester in step (ii), the reaction mixture is subjected to azeotropic dewatering.

DETAILED DESCRIPTION OF A PREFERRED EMBODIMENT

The malonic ester potassium salt of the formula (III) prepared in step (i) can be separated directly from the malonic ester of the formula (II), preferably by phase separation, in which case the malonic ester-potassium salt of the formula (III) remains in the aqueous phase and the malonic ester in the organic phase.

The malonic ester potassium salt is obtained in step (i) in such a purity that it can be used in step (ii) without further purification steps after separation from the reaction mixture. The compound is thus not used in solid form, but rather in dissolved form. In accordance with the invention the water still present from step (i) from the malonic ester potassium salt of the formula is removed by azeotropic dewatering of the aqueous phase comprising the malonic ester potassium salt of the formula (III). The dewatering is not effected until after addition of the chloroacetic ester of the formula (IV). Accordingly, the reaction in process step (ii) proceeds in substance.

Azeotropic dewatering is understood here to mean the removal of water by azeotropic distillation, preferably with the aid of a phase separator and in the presence of a suitable entraining agent which forms an azeotropic mixture with water, for example toluene or xylene.

After removal, the unconverted compound of the formula (II) is available without further workup for another reaction with potassium hydroxide, which constitutes a great advantage for continuous operation.

The process according to the invention has the advantage over the process described in WO 2009/036899 that it is possible in the reaction to dispense with expensive solvents which are difficult to remove and recover, such as dimethylformamide or dimethylacetamide, and that the malonic ester potassium salt is not isolated in solid form at any time.

Step (ii) is preferably performed in the presence of a small (catalytic) amount of water as a reaction mediator. Small amounts of water are understood, based on the total weight of the reaction mixture after the azeotropic dewatering, to mean the following amounts of water: about 0.8 to about 5.0 percent by weight (% by wt.). Amounts preferred in accordance with the invention are about 0.8 to about 4.0% by weight, about 0.8 to about 3.0% by weight, about 0.8 to about 2.0% by weight, and about 0.8 to about 1.5% by weight.

As a result of the presence of the small (catalytic) amount of water, the reaction in step (ii) is greatly accelerated and brought to complete conversion.

The chloroacetic ester of the formula (IV) unconverted in step (ii) is available without further workup for another reaction with the malonic ester potassium salt of the formula (III), which constitutes a great advantage for continuous operation.

The compound of the formula (V) obtained in step (ii) is obtained in such a purity that it can be used in step (iii) without intermediate isolation. However, it is preferable to subject the compound of the formula (V), before further reaction, to a distillation, phase separation and azeotropic drying.

Suitable solvents usable in step (i) are alcohols, especially methanol and ethanol. It is also possible to use other known alcohols. The solvent is used in such an amount that the stirrability of the reaction mixture remains good during reaction. Advantageously, step (i) is performed in a mixture of alcohol and water, especially methanol and water or ethanol and water. Usually, the water is introduced into the reaction mixture by using an aqueous potassium hydroxide solution. Should the water thus introduced be insufficient, it is of course possible to add water to the reaction mixture. The amount of water to be added may vary and can be determined easily by the person skilled in the art.

For the ring closure reaction in step (iii), it is possible to use any sodium alkoxide or potassium alkoxide, especially sodium methoxide or sodium ethoxide. For technical and economic reasons, it is preferable to use sodium alkoxides or potassium alkoxides which are present dissolved in the corresponding alcohol and are also commercially available (for example sodium methoxide dissolved in methanol), since there is then no need to use any other solvent.

The reactions in step (i) and step (ii) and the ring closure reaction of step (iii) can be performed at standard pressure. It is also possible to perform the reaction under reduced pressure or at elevated pressure (superatmospheric pressure).

The reactions in steps (i), (ii) and (iii) proceed at a suitable temperature which depends on the substrates used. Suitable temperatures can be determined in a simple manner by routine tests.

Step (i) can be performed, for example, at a temperature in the range from about −20° C. to about 20° C., preferably from about −10° C. to about 10° C. Particular preference is given to performing the reaction at a temperature in the range from about −5° C. to about 0° C., preferably under standard pressure.

Step (ii) can be performed, for example, at a temperature in the range from about 20° C. to about 200° C., preferably from about 60° C. to about 150° C. Particular preference is given to performing the reaction at a temperature in the range from about 80° C. to about 150° C., preferably under standard pressure.

Step (iii) can be performed, for example, at a temperature in the range from about 20° C. to about 120° C., preferably from about 20° C. to about 100° C. Particular preference is given to performing the reaction at a temperature in the range from about 20° C. to about 80° C., preferably under standard pressure.

In steps (i), (ii) and (iii) of the process according to the invention, the molar ratios of the compound of the formula (II) and potassium hydroxide, or of the compound of the formula (III) to the compound of the formula (IV), or of the compound of the formula (V) to the alkali metal alkoxide $ZOR^1$, may vary within wide ranges. They are generally not subject to any restriction.

In step (i), it is advantageous when the molar ratio of the compound of the formula (II) to potassium hydroxide is in the range from about 1.1 to about 10, especially in the range from about 1.5 to about 6. Preferably in accordance with the invention, the molar ratio is in the range from about 1.8 to 3.

In step (ii), it is advantageous when the molar ratio of the compound of the formula (IV) to the compound of the formula (III) is in the range from about 10 to about 1, especially in the range from about 8 to about 1. Preferably in accordance with the invention, the molar ratio is in the range from about 6 to 1.

In step (iii), it is advantageous when the molar ratio of the compound of the formula (V) to alkali metal alkoxide is in the range from about 0.9 to about 10, especially in the range from about 1 to about 5. Preferably in accordance with the invention, the molar ratio is in the range from about 1 to 2.

The reference to alkyl encompasses branched or unbranched alkyls. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl n-heptyl, n-octyl, n-nonyl, n-decyl, n-undecyl and n-dodecyl. Among these alkyl radicals, $C_1$-$C_6$-alkyl radicals are particularly preferred. Especially preferred are $C_1$-$C_4$-alkyl radicals, specifically methyl and ethyl.

The present invention is illustrated in detail by the examples which follow, though the examples should not be interpreted in such a manner as to restrict the invention.

PREPARATION EXAMPLE

Example 1

Preparation of sodium 4-(methoxycarbonyl)-5-oxo-2,5-dihydrofuran-3-olate and sodium 4-(ethoxycarbonyl)-5-oxo-2,5-dihydrofuran-3-olate Step (i): 481 g (3.00 mol) of diethyl malonate and 300 g of ethanol are initially charged and cooled to −5° C. Into this mixture are metered, at −5° C. to 0° C., 337 g (1.50 mol) of a 25% aqueous KOH solution within 2 hours. The mixture is stirred at 0° C. for 30 minutes and then ethanol is distilled off at 30° C. The two phases are separated at 5° C., and the upper organic phase, in which the unconverted diethyl malonate is present can be used directly for a further hydrolysis.

Step (ii): The aqueous phase is dewatered azeotropically at 30-50° C. under reduced pressure with 458 g (3.75 mol) of ethyl chloroacetate. After adding a further 458 g (3.75 mol) of ethyl chloroacetate and 9.4 g of water (0.8 percent by weight based on the mass of the reaction mixture) as a reaction mediator, the mixture is then heated to 105° C. and stirred at this temperature for a further 2.5 hours. Subsequently, ethyl chloroacetate is first distilled off at 60-80° C. and, after addition of 375 g of water, the remaining amount of ethyl chloroacetate is removed azeotropically. After cooling to 20° C., the aqueous phase is removed.

Step (iii): The organic phase is dried azeotropically with 50 g of xylene at 50-70° C. under reduced pressure and then admixed at 40-50° C. with 270 g (1.50 mol) of a 30% sodium methoxide solution in methanol within 1 hour. The mixture is then heated to 65° C. for 2 hours, then cooled to 20° C., stirred at this temperature for 1 hour and filtered. The residue is washed with 60 g of methanol as a displacement wash and dried under reduced pressure. This gives 209 g as a 7:3 mixture of sodium 4-(methoxycarbonyl)-5-oxo-2,5-dihydrofuran-3-olate and sodium 4-(ethoxycarbonyl)-5-oxo-2,5-dihydrofuran-3-olate. Based on potassium hydroxide used, this corresponds to an isolated yield of 76%.

$^1$H NMR ($D_2O$, 298K) δ: 3.73 s (3H), 4.42 s (2H) [main component]; 1.30 t (3H), 4.23 q (2H), 4.42 s (2H) [secondary component]

The invention claimed is:

1. A process for preparing a sodium or potassium salt of 4-hydroxy-2-oxo-2,5-dihydrofuran-3-carboxylic ester of formula (I)

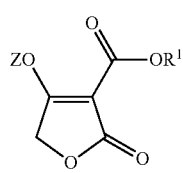
(I)

in which
Z is sodium or potassium, and
$R^1$ is $C_1$-$C_{12}$-alkyl,
comprising:
(i): reacting a symmetric malonic ester of formula (II)

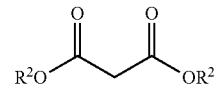
(II)

with potassium hydroxide to give the corresponding malonic ester potassium salt of formula (III)

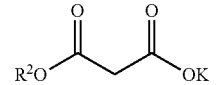
(III)

in which, in formulae (II) and (III),
$R^2$ is $C_1$-$C_{12}$-alkyl,
in a solvent;
(ii): reacting a malonic ester potassium salt of formula (III) with a chloroacetic ester of formula (IV)

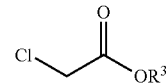
(IV)

in which
$R^3$ is $C_1$-$C_{12}$-alkyl,
to give a compound of formula (V)

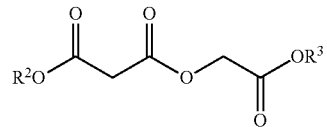
(V)

in which
$R^2$ has the definitions listed in relation to formula (III), and
$R^3$ has the definitions listed in relation to formula (IV),
(iii): reacting a compound of formula (V) with a sodium or potassium alkoxide of formula $ZOR^1$ in which
$R^1$ is $C_1$-$C_{12}$-alkyl, and
Z is sodium or potassium,
wherein after addition of the chloroacetic ester in (ii), the reaction mixture is subjected to azeotropic dewatering, in which, in (ii), from 0.8 to 5.0% by weight of water is added again to the reaction mixture after performance of the azeotropic dewatering,
and in which (ii) is performed in substance.

2. The process according to claim 1, in which an aqueous potassium hydroxide solution is used in (i), and in which the solvent in (i) is an alcohol.

3. The process according to claim 1, in which, on completion of conversion in (i), the malonic ester potassium salt of formula (III) is separated from unconverted malonic ester of formula (II) by phase separation before said malonic ester potassium salt is used in (ii).

4. The process according to claim 1, in which, in (iii), sodium methoxide, sodium ethoxide, potassium methoxide or potassium ethoxide is used.

5. The process according to claim 4, in which the sodium methoxide or the potassium methoxide is present dissolved in methanol, and the sodium ethoxide or the potassium ethoxide is present dissolved in ethanol.

6. The process according to claim 1, wherein Z is sodium.

7. The process according to claim 1, wherein Z is potassium.

8. The process according to claim 1, wherein R2 is methyl.

9. The process according to claim 1, wherein R2 is ethyl.

10. The process according claim 1, wherein R3 is methyl or ethyl.

11. The process according to claim 3, wherein the malonic ester potassium salt of formula (III) is used in step (ii) without further purification after the separation.

12. The process according to claim 1, wherein the malonic ester potassium salt of formula (III) is not isolated in solid form at any time.

13. The process according to claim 1, wherein dimethylformamide or dimethylacetamide are not used.

* * * * *